United States Patent [19]
Rozzell, Jr.

[11] Patent Number: 5,942,644
[45] Date of Patent: Aug. 24, 1999

[54] PRECURSORS FOR THE PRODUCTION OF CHIRAL VICINAL AMINOALCOHOLS

[75] Inventor: J. David Rozzell, Jr., Burbank, Calif.

[73] Assignee: BioCatalytics, Inc., Burbank, Calif.

[21] Appl. No.: 08/929,474

[22] Filed: Sep. 15, 1997

Related U.S. Application Data

[63] Continuation-in-part of application No. 08/863,900, May 27, 1997, Pat. No. 5,834,261.
[51] Int. Cl.$^6$ .......................... C07C 233/05; C07C 239/08
[52] U.S. Cl. .......................... 564/201; 564/148; 564/149; 564/150; 564/151; 564/170; 560/312
[58] Field of Search ........................... 564/172, 173, 564/189, 190, 201, 148, 149, 150, 151; 560/312

[56] References Cited

FOREIGN PATENT DOCUMENTS 01228468  3/1988  Japan.

OTHER PUBLICATIONS

Didier et al., "Chemo–enzymatic synthesis of 1,2– and 1,3–amino alcohols and their use in the enantioselective reduction of acetophenone and anti–acetophenone oxime methly ether with borane", Tetrahedron 47 (27): 4941–58 (1991).
Gotor, "Enzymic aminolysis, hydrzinolysis and oximolysis reactions", NATO ASI Ser., Ser. C 381 ; 199–208 (1992).
Pedrocchi–Fantoni et al., "Chiral amino alcohols from baker's yeast reduction of alpha keto acid derivatives", Gazz. Chim. Ital. 122 (12) : 499–502 (1992).
Geissman, T.A., Rearrangements Involving Electron–deficient Nitrogen in Principles of Organic Chemistry (W. H. Freeman & Co., 1962), pp. 674–675.
Stager et al, Tetrahedron, vol. 39, No. 10, pp. 1829–1836, 1983.
Fulop et al, J. Heterocyclic Chem., vol. 27, pp. 951–955, 1990.
Fulop et al, J. Chem. Soc, Perk. Trans., 1, pp. 2043–2048, 1984.
Quiros et al., Enantioselective reduction of β–keto amides by the fungus *Mortierella isabellina*, 1997, pp. 3035–3038.
Ito, et al., "Highly Anti–Diastereoselective Reduction of 2–Alkyl–3–Oxo Amides By Potassium Triethylborohydride," Tetrahedron Letters, vol. 26, No. 38, pp. 4643–4646, 1985.
1997 Physician's Desk Reference pp. 1670–1673.
1992 C. Bull et al in "Biocatalytic Production of Amino Acids and Derivatives". pp. 255–256.
1992. Preparative Biotransformations, S.M. Roberts, Ed Chapter 2.
1996 A.U. Saksena et al, *Tetrahedron Letters*, 37 pp. 5657–5660.
1948 Tullar, B.F., *J. Am. Chem. Soc*, 70 2067–2078.
1986 D. Buisson and R. Azerad, *Tetrahedron Letters*, 27, 2631–2634.
1990 S. Servi, *Synthesis*, pp. 1–25.
1985 D. Seebach et al. *Organic Synthesis*, 63, 1–9.
1987 D.W. Brooks and K.W. Woods, *J. Org. Chem.*, 53, 5215–5219.
1988 A. Faure and H. Veschambre, *J. Org. Chem.*, 52, 5215–5219.
1978 M. Bucciarelli et al, *J. Chem. Soc. Chem Comm.*, pp. 456–457.
1984 U. Ureslich in *Biotransformations*, vol. 6a, Chapter O.
1980 Z. Shaked and G.M. Whitesides, *J. Am. Chem. Soc.*, 102, 7104–7105.
1984 J. B. Jones and T. Takemura, *Canadian J. Chem*, 62, 77–80.
1949 E.S. Wallis and J. F Lane *Organic Reactions* III, Chapter 7, pp. 207–306.
1969 P.A S. Smith, *Trans. N.Y. Acad. Sci*, 31, 504–515.
1973 S. Simons Jr., *J. Org Chem.* 38 414–416.
1976 W.L.F. Armarego et al, *J. Chem Soc. Perkin Trans I.*, 2229–2237.
1974 S. Bittner et al, *Tet. Lett.* 23, 1965–1968.
1974 L. Bauer and O. Exner, *Angew. Chem. Int. Ed.*, 13, 376–384.
1946 P.A.S. Smith, *Organic Reactions. III*, Chapter 9, pp. 337–338.
1948 J. H. Saunders and R. J. Slocombe, *Chem. Rev.* 43, 203–218.
1971 D. V. Banthorpe in "The Chemistry of the Azido Group ", Chapter 7, pp.397–405.
1980 J. D. Warren and J.B. Press, *Synth. Comm., 10* 107–110.

*Primary Examiner*—Shailendra Kumar
*Attorney, Agent, or Firm*—Christie, Parker & Hale, LLP

[57] ABSTRACT

The disclosure describes new compositions of matter useful for the preparation of optically-active vicinal aminoalcohols. The compositions are chiral β-hydroxycarboxamides, β-hydroxyhydraxides, and β-hydroxyhydroxamic acids.

33 Claims, No Drawings

PRECURSORS FOR THE PRODUCTION OF CHIRAL VICINAL AMINOALCOHOLS

CROSS-REFERENCE TO RELATED APPLICATION

This application is a continuation-in-part of U.S. patent application Ser. No. 08/863,900, entitled "Method for the Production of Chiral Vicinal Aminoalcohols," filed May 27, 1997, now U.S. Pat. No. 5,834,261.

FIELD OF THE INVENTION

The present invention relates to novel compositions of matter which are key precursors for the production of chiral vicinal aminoalcohols.

BACKGROUND

Chiral vicinal aminoalcohols are important intermediates in the synthesis of various pharmaceutical products and product candidates, yet the preparation of these compounds remains a significant synthetic challenge to chemists. Vicinal aminoalcohols which contain chiral centers at either the carbon bearing the amino group, the carbon bearing the hydroxy group, or at both carbons are the subject of the present invention. Gaining control over the stereochemistry of these chiral centers at reasonable cost is the key to the successful production of these important chemical compounds.

One example of an important chiral vicinal aminoalcohol is found in SCH 56592, described in Tetrahedron Letters 37, 5657 (1996) and references therein, hereby incorporated by reference. SCH 56592 is a potent antifungal compound. A key component in the synthesis of SCH 56592 is the chiral vicinal aminoalcohol moiety (3S,4S)-3-amino-4-hydroxypentane. No efficient and cost effective route for its synthesis has been described.

Another example of an important chiral vicinal aminoalcohol is found in the drug Crixivan, an HIV-protease inhibitor produced by Merck & Co. This compound is one of the most potent inhibitors of the AIDS virus yet discovered. A key intermediate in its synthesis is the chiral vicinal aminoalcohol (1S,2R)-1-amino-2-indanol (1997 Physicians' Desk Reference, Medical Economics Company, Montvale, N.J., pp. 1670–1673).

There are a number of additional examples of important molecules which contain chiral aminoalcohols, including ephedrine, pseudoephedrine, norephedrine, pseudonorephedrine, epinephrine, norepinephrine, isoserinol, isoleucinol, histidinol, 2-aminocyclopentanol, 2-aminocyclohexanol, phenylglycinol, and many others. Methods for the production of compounds which contain chiral aminoalcohol functionality tend to be specific for a given molecule or small group of related molecules. For example, several routes exist for the production of ephedrine (see, for example Fodor, Recent Develop. Chem. Nat. Carbon Compounds 1, 15–160 (1965). However, these methods are not broadly generalizable to many other chiral vicinal aminoalcohols. The enzyme serine hydroxymethyltransferase can catalyze the production of certain chiral vicinal aminoalcohols such as threonine and phenylserine, but only with severe structural limitations; there is an absolute requirement for glycine as a substrate, limiting carbon-1 to being only a carboxyl group. In addition, only certain aldehydes are accepted as substrates to condense with glycine. Furthermore, a mixture of stereoisomers is invariably obtained, making the production and recovery of highly pure chiral vicinal aminoalcohols difficult. (See C. Bull et al. in Biocatalytic Production of Amino Acids and Derivatives, D. Rozzell and F. Wagner, Eds., Hanser Publishers, Munich, (1992) pp. 255–256.) Often, classical resolution procedures are used due to the absence of any better method, resulting in the loss of 50% or more of the starting material (see, for example Tullar, J. Am. Chem. Soc. 70, 2067 (1948) which describes the resolution of D,L-epinephrine). A general method for the production of molecules of high optical purity incorporating a chiral vicinal aminoalcohol would facilitate the production of this important class of pharmaceutical intermediates and would be greatly desired.

SUMMARY OF THE INVENTION

The present invention is directed to a composition comprising a compound having a formula selected from the group consisting of:

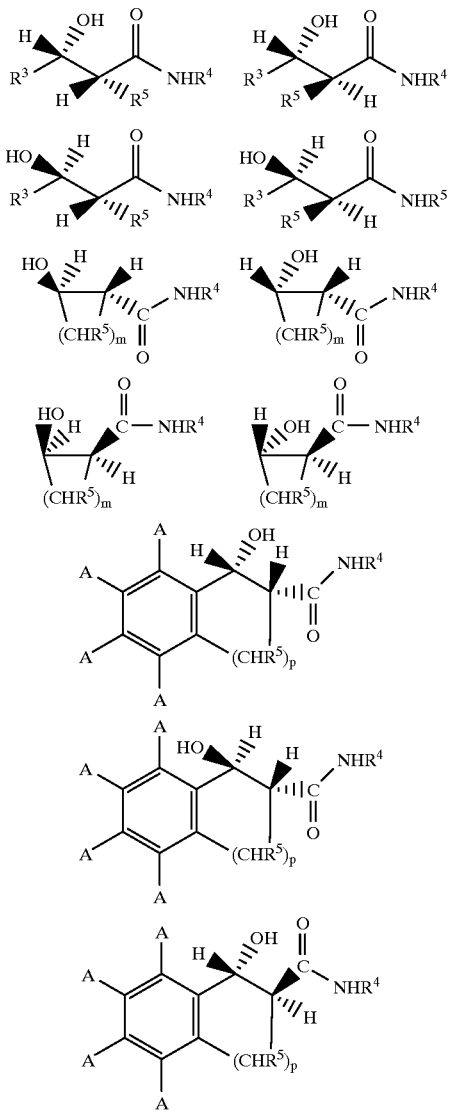

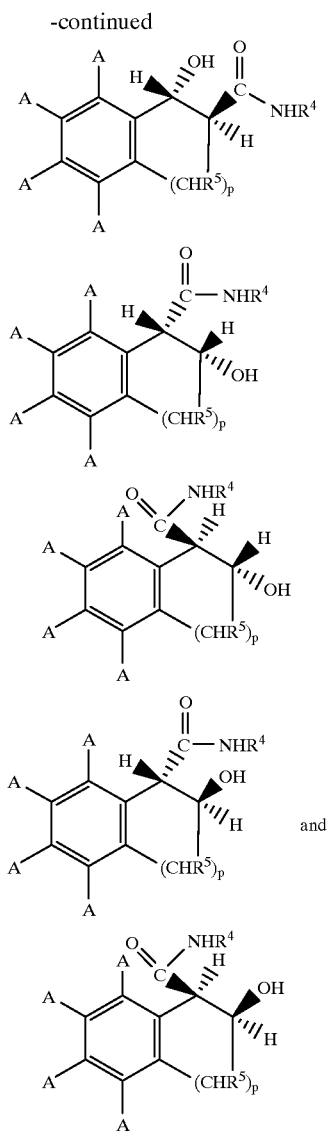

wherein:

R³ is selected from the group consisting of alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic;

R⁴ is selected from the group consisting of H, OH, and NH₂;

R⁵ is selected from the group consisting of hydrogen, alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic;

A is selected from the group consisting of H, F, Cl, Br, I, OH, OCH₃, alkyl, carboxy-substituted alkyl, hydroxy-substituted alkyl, halogen-substituted alkyl, aryl, carboxy-substituted aryl, hydroxy-substituted aryl, halogen-substituted aryl, and heterocyclic;

m is a number ranging from 1 to 6; and p is a number ranging from 0 to 6.

The compound comprises at least 75% of a single stereoisomer, more preferably at least 90% of a single stereoisomer, and still more preferably at least 98% of a single stereoisomer.

In the above compositions, preferably p is 1 or 2 and m is 3 or 4. R⁵ is preferably selected from the group consisting of alkyl, aryl, benzyl and alkenyl. R³ is preferably selected from the group consisting of alkyl, aryl, benzyl and alkenyl.

DETAILED DESCRIPTION OF THE INVENTION

This invention describes key intermediates useful for the production of chiral vicinal aminoalcohols. An important aspect of this invention is the generality with which these intermediates described herein may be employed to produce a range of chiral vicinal aminoalcohols, both cyclic and acyclic, with the ability to produce any of the 4 possible stereoisomers in high stereochemical purity.

Central to the production of these intermediates is the novel combination of two steps, each of which proceeds with a well-defined and controllable stereochemical outcome. This method is described in U.S. patent application Ser. No. 08/836,900. The first step is the stereoselective reduction of the keto group of a β-ketoacid, β-ketoester, β-ketocarboxamide, β-ketocarboxylic hydroxamic acid, or β-ketocarboxylic hydrazide (and, in the case of the β-ketoester or β-ketoacid, conversion of the β-hydroxyester or β-hydroxyacid to the corresponding carboxamide, hydroxamic acid or hydrazide derivative); this reaction provides for control of stereochemistry at both the C-2 and C-3 positions of the β-ketoacid or derivative, producing a product having two chiral centers. Stereoselective reduction of the β-ketoacid or derivative is effected by any of a range of microorganisms which are able to reduce carbonyl groups in the presence of a carbon source such as glucose or other carbohydrates. This reaction may be carried out to generate a single diastereomer of the four possibilities in high optical purity, depending on the choice of organism or enzyme for the reduction. The second step is the stereospecific rearrangement of the resulting 2-substituted-3-hydroxycarboxamide, carboxylic hydrazide, or carboxylic hydroxamic acid to the corresponding aminoalcohol, resulting in a chiral vicinal aminoalcohol with control of stereochemistry at one or two chiral centers. This rearrangement occurs with retention of stereochemistry at the carbon bearing the carbonyl group.

The β-ketoacid or its derivative may be derived from an inexpensive precursor such as ethyl acetoacetate or another acetoacetic ester, or the esters of related β-ketoacids such as a 2-alkyl substituted acetoacetate, cyclohexanone-2-carboxylate, cyclopentanone-2-carboxylate, 1-indanone-2-carboxylate, 2-indanone-1-carboxylate, 1-tetralone-2-carboxylate, 2-tetralone-1-carboxylate, and the like. Both simple β-ketoesters such as esters of acetoacetate, 3-ketopentanoate, 4-phenylacetoacetate, and various 2-alkyl-substituted β-ketoesters may be reduced with control of stereochemistry at, depending on the starting material, either the 3-position or both the 2 and 3 positions. Substituents which may be present at the 2-position in the practice of this invention include methyl, ethyl propyl, isopropyl, butyl, isobutyl, pentyl, isopentyl, hexyl, octyl, vinyl, propargyl, allyl, thiophenyl, thioalkyl, phenyl, benzyl, furoyl, imidazoyl, carboxymethyl, carboxyethyl, halomethyl haloethyl, halopropyl, phosphoalkyl, and the like. Cyclic β-ketoacid derivatives, which upon reduction give rise to two chiral centers, are also useful intermediates for the production of chiral vicinal aminoalcohols. Useful cyclic β-ketoacid derivatives include cyclohexanone-2-carboxylate, cyclopentanone-2-carboxylate, 1-indanone-2-carboxylate, 2-indanone-1-carboxylate, 1-tetralone-2-carboxylate, 2-tetralone-1-carboxylate, and the like.

Conversion of the chiral β-hydroxyester or β-hydroxyacid to the corresponding amide, hydroxamic acid or hydrazide derivative may be accomplished by straightforward chemical methods well-known to those skilled in the art. For example, heating of a chiral β-hydroxyester with ammonia, hydrazine, or hydroxylamine in ethanol produces the corresponding amide, hydrazide, or hydroxamic acid in high yield. Alternatively, conversion of the ester to the amide, hydroxamic acid or hydrazide may be accomplished by enzymatic catalysis. Esterase, lipase, protease, and amidase enzymes, which can catalyze the hydrolysis of esters in the presence of water, will catalyze conversion of the ester to the amide, hydroxamic acid or hydrazide when ammonia, hydroxylamine or hydrazine are present as nucleophiles. The enzymatic conversion has the added advantage that it often can be carried out under very mild conditions (e.g. ambient temperature and pressure). Further, the enzyme can provide additional stereoselection in the conversion of the ester to its corresponding amide, hydroxamic acid or hydrazide derivative, further improving the enantiopurity of the final product in cases where this is desired.

As a further embodiment of this invention, the β-ketoacid or β-ketoester may be first converted into its amide, hydroxamic acid, or hydrazide derivative, and the stereoselective reduction carried out on the corresponding amide, hydroxamic acid, or hydrazide derivative to produce the optically-active, chiral β-hydroxycarboxamide, β-hydroxy hydrazide, or β-hydroxy hydroxamic acid. For example, acetoacetamide or a 2-substituted acetoacetamide may be subjected to the stereoselective reduction by a microorganism or a dehydrogenase, followed by the Hofmann rearrangement on the 2-substituted-3-hydroxybutyramide to give the chiral vicinal aminoalcohol. Similarly, the hydroxamic acid or hydrazide derivatives of a 2-substituted (or unsubstituted)

Stereoselective reduction may be conveniently carried out using whole cells or isolated enzymes. In the case of whole cells, organisms useful in the practice of this invention are described in Preparative Biotransformations (S. M. Roberts, editor), Chapter 2, John Wiley & Sons, Chichester, U.K. (1996) and references therein; D. Buisson and R Azerad, Tetrahedron Lett., (1986) 27, 2631, and references therein; S. Servi, *Synthesis,* 1 (1990) and references therein; D. Seebach et al., *Organic Synthesis* 63, 1 (1985) and references therein; D. W. Brooks and K. W. Woods, *J. Org. Chem.* 52, 2036 (1987) and references therein; A. Fauve and H Veschambre, *J. Org. Chem.* 53, 5215 (1988) and references therein; Bucciarelli et al., *J. Chem. Soc. Chem. Comm.,* 456 (1978) and references therein; K. Kieslich in *Biotransformations,* Eds. H. J. Rehm and G. R. Reed, volume 6a, VCH, Weinheim (1984) and references therein; all hereby incorporated by reference; and include *Saccharomyces cerevisiae, Geotrichum candidum, Colletotrichum gloeosporioides, Rhizopus arrhizus, Aspergillus niger, Mortierella isabellina,* and other microorganisms.

It is also possible to use isolated dehydrogenase enzymes, either as crude, partially purified, or pure preparations in the practice of this invention. Dehydrogenases useful in the practice of this invention may be isolated and purified, if desired, from microorganisms capable of effecting the stereoselective reduction. The purification of the dehydrogenase enzymes may be accomplished by techniques well known to those skilled in the art. Some examples of purification methods for enzymes may be found in *Methods in Enzymology,* 22 (1971) and references therein, hereby incorporated by reference. In the case of isolated enzymes, the nicotinamide cofactor is recycled using any of a number of recycling schemes known in the prior art [See, for example, Preparative *Biotransformations* (S. M. Roberts, editor), 3.1.1–3.1.6, John Wiley & Sons, Chichester, U.K. (1996) and references therein; Z. Shaked and G. M. Whitesides, *J. Am. Chem. Soc.* 102, 7104–5 (1980) and references therein; J. B. Jones and T. Takamura, *Can. J. Chem.* 62, 77 (1984); all hereby incorporated by reference.] These enzymes may be used in solution or, if desired, as immobilized enzymes in accord with the practice of this invention. A number of methods of immobilization for both whole cells containing enzymes and for isolated enzymes are known in the prior art and may be used in the practice of this invention. One example of an immobilized enzyme system is described by Weetall et al., *Methods in Enzymology* 34, 59–72 (1974) which is hereby incorporated by reference. In this method enzymes may be immobilized on a porous glass or ceramic support which has been activated with glutaraldehyde. Other methods for immobilization of both cells and enzymes which may be used in the practice of this invention are described in *Methods in Enzymology* 44 (1976), K. Mosbach editor, *Immobilization of Enzymes and Cells,* Gordon F. Bickerstaff, ed., Humana Press, Totowa, N.J. (1997) and in *Biocatalytic Production of Amino Acids and Derivatives,* D. Rozzell and F. Wagner, Eds., Hanser Publishers, Munich, (1992) pp. 279–319.

An important application of the optically-active, chiral hydroxycarboxamide, hydroxy hydrazide, and hydroxy hydroxamic acid compounds, which are the subject of this invention, derives from their ability to be converted into optically-active chiral vicinal aminoalcohols in a single step. For example, the vicinal hydroxycarboxamide may be converted into a chiral vicinal aminoalcohol via the Hofmann rearrangement. Similarly, the hydroxy hydrazide and hydroxy hydroxamic acid may be converted to the corresponding chiral vicinal aminoalcohols using the Curtius or Lossen rearrangements, respectively.

The stereospecific rearrangement may be carried out on the carboxamide via the Hofmann-type rearrangement [E. S. Wallis and J. F. Lane, *Organic Reactions* III,267 (1949) and references therein; P. A. S. Smith, *Trans. N.Y. Acad. Sci.* 31, 504 (1969) and references therein; S. Simons, *J. Org Chem.* 38, 414 91973) and references therein; W. L. F. Armarego et al, *J. Chem. Soc. Perkin Trans.* I, 2229 (1976) and references therein; all hereby incorporated by reference]; on the hydroxamic acid via the Lossen rearrangement [S. Bittner et al (*Tet. Lett.* 23, 1965–8 (1974) and references therein; L. Bauer and O. Exner, *Angew. Chem. Int. Ed.* 13, 376 (1974) and references therein; all hereby incorporated by reference]; or on the hydrazide via the Curtius rearrangement [P. A. S. Smith, *Organic Reactions* III, 337 (1946) and references therein; J. H. Saunders and R. J. Slocombe, *Chem. Rev.* 43, 205 (1948) and references therein; D. V. Banthorpe in *The Chemistry of the Azido Group,* S. Patai Ed., Interscience, New York, 1971, pp. 397–405 and references therein; J. D. Warren and J. D. Press, *Synth. Comm.* 10, 107 (1980) and references therein; all hereby incorporated by reference].

As an example of the practice of this invention, (3S,4S)-3-amino-4-hydroxypentane, the key component of SCH 56592, may be produced either from the precursor (2S,3S)-2-ethyl-3-hydroxybutyric hydrazide via the Curtius rearrangement, the precursor (2S,3S)-2-ethyl-3-hydroxybutyric hydroxamic acid via the Lossen rearrangement, or the precursor (2S,3S)-2-ethyl-3-hydroxybutyramide via the Hofmann rearrangement. The hydrazide, hydroxamic acid, or amide compounds permit efficient and cost effective synthesis of the corresponding chiral vicinal aminoalcohol. The desired chiral vicinal aminoalcohol is produced from the following simple and inexpensive chemical building blocks: ethyl 2-ethylacetoacetate (produced from ethyl acetoacetate and ethyl bromide), ammonia (or hydroxylamine or hydrazine), and bromine (or benzoyl chloride or sodium nitrite).

Similarly, the chiral vicinal aminoalcohol (1S,2R)-1-amino-2-indanol, a key intermediate in the production of the HIV-inhibitor Crixivan, may be produced from the hydrazide of (1S,2R)-1-carboxy-2-hydroxyindane by reaction with a solution of sodium nitrite in 5% $H_2SO_4$ via the Curtius rearrangement.

The following example is illustrative of the straightforward application of this invention. Ethyl 2-ethylacetoacetate is added to a culture of *Colletotrichum gloeosporoides* ATCC 16330, which had been cultivated on glucose as a carbon source. After 48 hours of agitation, the culture broth is filtered, extracted with ethyl acetate, and evaporated to leave (2S,3S)-ethyl 2-ethyl-3-hydroxybutyrate as a yellowish oil. This product is warmed with hydrazine in ethanol to produce the hydrazide derivative. The resulting hydrazide is isolated and treated with sodium nitrite in 5% sulfuric acid to produce (2S,3S)-2-amino-3-hydroxypentane via the Curtius rearrangement. The aminoalcohol may be recovered conveniently by extraction into an organic solvent such as ethyl acetate or methyl t-butyl ether after basification of the reaction mixture.

In cases where the alcohol is the only chiral center, the sequence is similarly effective, maintaining complete control over the chirality of the alcohol after stereospecific reduction through the rearrangement of the amide, hydrazide, or hydroxamic acid.

The invention will now be further described by the following examples, which are given here for illustrative purposes only and are not intended to limit the scope of the invention.

EXAMPLE 1
Production of ethyl (2R,3S)-2-ethyl-3-hydroxybutyrate

Twenty grams of bakers' yeast (Sigma Chemical Company, *Saccharomyces cerevisiae*, type II) are suspended in a solution of 30 grams of sucrose in water in a conical flask, and the mixture is placed in an orbital shaker chamber maintained at 220 rpm and 30° C. for 30 minutes to initiate fermentation. Two grams of ethyl 2-ethyl acetoacetate are dissolved in 2 ml of 95% ethanol, the resulting solution is added to the fermenting yeast, and shaking is resumed. The reaction is followed by TLC (staining with phosphomolybdic acid in ethanolic sulfuric acid) to monitor the consumption of starting material and the production of product alcohol. After approximately 48 hours the reaction is judged complete, and the reaction is terminated by removing the flask from the shaker and adding 20–30 grams of Celite to the reaction mixture. The resulting suspension is suction filtered through a pad of Celite, and the clear yellow filtrate is extracted with ethyl acetate (4×200 ml). The extracts are combined, dried over $MgSO_4$, filtered, and rotary evaporated to leave 1.6 grams of a yellowish oil containing (2R,3S)-2-ethyl-3-hydroxybutyrate as the major product (80%) and (2S,3S)-2-ethyl-3-hydroxybutyrate (20%) as the minor product as judged by chiral chromatography.

EXAMPLE 2
Production of octyl (2R,3S)-2-ethyl-3-hydroxybutyrate

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of octyl 2-ethyl acetoacetate is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.8 grams of octyl (2R,3S)-2-ethyl-3-hydroxybutyrate as a yellowish oil (>96% enantiomeric excess as judged by chiral chromatography).

EXAMPLE 3
Production of (2R,3S)-ethyl 2-allyl-3-hydroxybutyrate

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of ethyl 2-methyl acetoacetate is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.6 grams of a yellow oil containing (2R,3S)-2-ethyl-3-hydroxybutyrate as the major product (75%) and (2S,3S)-2-ethyl-3-hydroxybutyrate (25%) as the minor product as judged by chiral chromatography.

EXAMPLE 4
Production of ethyl (2S,3S)-2-ethyl-3-hydroxybutyrate

*Colletotrichum gloeosporoides* (MMP 3233) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of ethyl 2-ethyl acetoacetate is dissolved in 2 ml of 95% ethanol the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.7 grams of (2S,3S)-2-ethyl-3-hydroxybutyrate as a yellow oil. The chiral purity of the product is greater than 98% as judged by chiral chromatography.

EXAMPLE 5

Alternative production of ethyl (2S,3S)-2-ethyl-3-hydroxybutyrate

Rhizopus arrhizus (ATCC 11145) is cultured according to the method of Buisson and Azerad (Tet. Lett. 27, 2631–2634 (1986), herein incorporated by reference) in one liter of a medium of glucose (30 grams), KH$_2$PO$_4$ (1 gram), K$_2$HPO$_4$ (2 grams), corn steep liquor (10 grams) MgSO$_4$.7H$_2$O (0.5 gram), NaNO$_3$ (2 grams), FeSO$_4$.7H$_2$O (0.02 gram), and KCl (0.5 gram) with rotary shaking at 25° C. Two grams of ethyl 2-ethyl acetoacetate is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.6 grams of (2S,3S)-2-ethyl-3-hydroxybutyrate as a yellow oil. The chiral purity of the product is shown to be greater than 98% as judged by chiral chromatography.

EXAMPLE 6

Alternative production of ethyl (2S,3S)-2-ethyl-3-hydroxybutyrate

Two grams of ethyl 2-ethyl acetoacetate are dissolved in 2 ml of 95% ethanol, and the resulting solution is added to a solution of alcohol dehydrogenase (500 units from Rhizopus arrhizus (ATCC 11145) containing potassium phosphate buffer, 100 mM, pH 7.0. NAD+ (100 mg) is added to the solution along with 1 gram of sodium formate and 100 units of formate dehydrogenase (Boehringer Mannheim). for recycling of the NAD+ cofactor. The reaction is followed by TLC (staining with anisaldehyde) to monitor the consumption of starting material and the production of product alcohol. After approximately 48 hours the reaction is judged complete, and the reaction is terminated by removing from the shaker. The resulting solution is extracted with ethyl acetate (4×200 ml). The extracts are combined, dried over MgSO$_4$, filtered, and rotary evaporated to leave 1.8 grams of (2S,3S)-2-ethyl-3-hydroxybutyrate as a light yellow oil. The chiral purity of the product is greater than 99% as judged by chiral chromatography.

EXAMPLE 7

Production of (1S,2R)-ethyl 2-hydroxycyclopentanecarboxylate

Twenty-five grams of bakers' yeast (Saccharomyces cerevisiae, Sigma Chemical Company, type II) are suspended in 100 ml of sterilized tap water in a conical flask, and the mixture is placed on an orbital shaker (220 rpm) at 30° C. for 1 hour to activate the yeast. One gram of ethyl 2-oxocyclopentanecarboxylate is added, shaking is resumed, and progress of the reaction is monitored by TLC (staining with anisaldehyde). After approximately 100 hours the reaction is judged complete, and the reaction is terminated by removing from the shaker and adding 20–30 grams of Celite. The resulting suspension is suction filtered through a pad of Celite and the clear yellow filtrate is extracted with diethyl ether (4×100 ml). The extracts are combined, dried over MgSO$_4$, filtered, and rotary evaporated to leave 0.7 grams of octyl (1R,2S)-ethyl 2-hydroxycyclopentanecarboxylate as a yellowish oil (70% yield).

EXAMPLE 8

Production of (1R,2S)-ethyl 2-hydroxycyclohexanecarboxylate

Twenty-five grams of bakers' yeast (Saccharomyces cerevisiae, Sigma Chemical Company, type II) are suspended in 100 m of sterilized tap water in a conical flask, and the mixture is placed on an orbital shaker (220 rpm) at 30° C. for 1 hour to activate the yeast. One gram of ethyl 2-oxocyclohexanecarboxylate is added, shaking is resumed, and progress of the reaction is monitored by TLC (staining with anisaldehyde). After approximately 100 hours the reaction is judged complete, and the reaction is terminated by removing from the shaker and adding 20–30 grams of Celite. The resulting suspension is suction filtered through a pad of Celite and the clear yellow filtrate is extracted with diethyl ether (4–100 ml). The extracts are combined, dried over MgSO$_4$, filtered, and rotary evaporated to leave 0.6 grams of octyl (1R,2S)-ethyl 2-hydroxycyclohexanecarboxylate as a yellowish oil (60% yield).

EXAMPLE 9

Production of (1S,2S)-ethyl 2-hydroxycyclopentanecarboxylate

Geotrichum candidum (ATCC 34614) is cultured according to the method of Buisson and Azerad (Tet. Lett. 27, 2631–2634 (1986), herein incorporated by reference) in one liter of a medium of glucose (30 grams), KH$_2$PO$_4$ (1 gram), K$_2$HPO$_4$(2 grams), corn steep liquor (10 grams) MgSO$_4$.7H$_2$O (0.5 gram), NaNO$_3$ (2 grams), FeSO$_4$.7H$_2$O (0.02 gram), and KCl (0.5 gram) with rotary shaking at 25° C. Two grams of ethyl 2-oxocyclopentanecarboxylate are dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.5 grams of (1S,2S)-2-hydroxycyclopentanecarboxylate as a yellow oil. The chiral purity of the product is greater than 99% as judged by chiral chromatography.

EXAMPLE 10

Production of (1S,2S)-ethyl 2-hydroxycyclohexanecarboxylate

Geotrichum candidum (ATCC 34614) is cultured according to the method of Buisson and Azerad (Tet. Lett. 27, 2631–2634 (1986), herein incorporated by reference) in one liter of a medium of glucose (30 grams), KH$_2$PO$_4$ (1 gram), K$_2$HPO$_4$ (2 grams), corn steep liquor (10 grams) MgSO$_4$.7H$_2$O (0.5 gram), NaNO$_3$ (2 grams), FeSO$_4$.7H$_2$O (0.02 gram), and KCl (0.5 gram) with rotary shaking at 25° C. Two grams of ethyl 2-oxocyclohexanecarboxylate are dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of (1S,2S)-ethyl 2-hydroxycyclohexanecarboxylate as a yellow oil. The chiral purity of the product is greater than 99% as judged by chiral chromatography.

EXAMPLE 11
Production of ethyl S-3 hydroxybutyrate

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of ethyl acetoacetate is dissolved in 2 ml of 95% ethanol the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.5 grams of a light yellow oil containing (S)-ethyl 3-hydroxybutyrate as the major product as judged by chiral chromatography.

EXAMPLE 12
Production of (R)-ethyl 3-hydroxybutyrate

*Geotrichum candidum* (ATCC 34614) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of ethyl acetoacetate are dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of (R)-ethyl 3-hydroxybutyrate as a yellow oil.

EXAMPLE 13
Production of (2S,3S)-2 ethyl-3-hydroxybutyramide by microbial reduction of the corresponding 2-ethylacetoacetamide

*Geotrichum candidum* (ATCC 34614) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-ethyl-3-ketobutyramide are dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the dear yellow filtrate is extracted with ethyl acetate (4×200 ml). The extracts are combined, dried over $MgSO_4$, filtered, and rotary evaporated to leave 1 gram of (2S,3S)-2 ethyl-3-hydroxybutyramide as a yellowish solid.

EXAMPLE 14
Production of S-3 hydroxybutyramide

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of acetoacetamide is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the dear yellow filtrate is extracted with ethyl acetate (4×200 ml). The extracts are combined, dried over $MgSO_4$, filtered, and rotary evaporated to leave 1.4 grams of (S)-3-hydroxybutyramide as a light yellow solid.

EXAMPLE 15
Production of the hydroxamic acid of (2S,3S)-2 ethyl-3-hydroxybutyrate (2S,3S)-Ethyl 2 ethyl-3-hydroxybutyrate (1 gram) is dissolved in 5 ml of absolute ethanol, followed by the addition of 0.5 gram of hydroxylamine. The solution is heated to reflux, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (2S,3S)-2 ethyl-3-hydroxybutyrate.

EXAMPLE 16
Enzymatic production of the hydroxamic acid of (2S,3S)-2 ethyl-3-hydroxybutyrate (2S,3S)-Ethyl 2 ethyl-3-hydroxybutyrate (1 gram) is dissolved in 5 ml of t-butyl methyl ether, followed by the addition of 0.5 gram of hydroxylamine. Lipase from *Candida rugosa* (0.5 g, Sigma L1754) is added, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (2S,3S)-2 ethyl-3-hydroxybutyrate.

EXAMPLE 17
Alternative production of the hydroxamic acid of (2S,3S)-2 ethyl-3-hydroxybutyrate by microbial reduction of the corresponding hydroxamic acid of 2-ethylacetoacetate

*Geotrichum candidum* (ATCC 34614) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-ethylacetoacetate hydroxamic acid, produced by the reaction of ethyl acetoacetate with hydroxylamine, are dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of (2S,3S)-2 ethyl-3-hydroxybutyrate hydroxamic acid as a yellowish solid.

EXAMPLE 18
Conversion of (2S,3S)-ethyl 2-ethyl-3-hydroxybutyrate to the hydrazide derivative (2S,3S)-Ethyl 2 ethyl-3-hydroxybutyrate (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (2S,3S)-2 ethyl-3-hydroxybutyrate.

EXAMPLE 19
Microbial production of the hydrazide of (2S,3S)-2 ethyl-3-hydroxybutyrate by stereospecific reduction of 2-ethylacetoacetate hydrazide

*Geotrichum candidum* (ATCC 34614) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-ethylacetoacetate hydrazide, produced by the reaction of ethyl 2-ethylacetoacetate with hydrazine, are dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of (2S,3S)-2 ethyl-3-hydroxybutyrate hydrazide as a yellowish solid.

EXAMPLE 20
Conversion of (2S,3S)-ethyl 2-ethyl-3-hydroxybutyrate to the amide derivative (2S,3S)-Ethyl 2 ethyl-3-hydroxybutyrate (1 gram) is dissolved in 5 ml of absolute ethanol followed by the addition of 0.5 gram of gaseous ammonia. The solution is kept in a stoppered flask, and the progress of the reaction is followed by thin layer chromatography. After the reaction is judged complete, the ethanol is evaporated and the resulting residue redissolved in ethyl acetate. Ammonia is removed by extraction with 1% HCl, and the ethyl acetate solution is dried over $MgSO_4$, filtered, and rotary evaporated to leave 0.7 grams of (2S,3S)-2 ethyl-3-hydroxybutyramide.

EXAMPLE 21
Production of (2R,3S)-2-amino-3-hydroxybutane by Hofmann Reaction

Ten grams of (2R,3S)-2-methyl-3 hydroxybutyramide are dissolved in 250 ml of 0.03 M NaOH and added slowly to a solution 25 grams of bromine in 300 ml of 0.03 M NaOH. The mixture is warmed with stirring until the reddish brown color disappeared. The solution is then cooled, extracted with methyl t-butyl ether×250 ml), and the extracts dried over $MgSO_4$, filtered, and the solvent removed by rotary evaporation. The product (2R,3S)-2-amino-3 hydroxybutane is isolated as a light yellow oil.

EXAMPLE 22
Production of (2R,3S)-2-amino-3-hydroxybutane by Lossen Rearrangement Ten grams of (2R,3S)-2-methyl-3 hydroxybutyrohydroxamic acid are reacted with benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (2R,3S)-2-amino-3 hydroxy-butane is isolated as a light yellow oil.

EXAMPLE 23
Production of (3S,4S)-3-amino-4-hydroxypentane by Lossen Rearrangement Ten grams of (2S,2S)-2-methyl-3-hydroxypentanohydroxamic acid are reacted with benzoyl chloride under Schotten-Bauman conditions, followed by warming to reflux. Reaction progress is monitored by thin layer chromatography. The solution is then cooled to room temperature, extracted with methyl t-butyl ether×250 ml), and the extracts dried over $MgSO_4$, filtered, and the solvent removed by rotary evaporation. The product (3S,4S)-3-amino-4-hydroxypentane is isolated as a light yellow oil.

EXAMPLE 24
Production of (3S,4S)-3-amino-4-hydroxypentane by a modified Lossen Rearrangement Ten grams of (2S,3S)-2-methyl-3-hydroxypentanohydroxamic acid are reacted with equimolar amounts of diethyl azodicarboxylate and triphenylphosphine in tetrahydrofuran at room temperature using the procedure of Bittner, Grinberg and Kartoon (Tet. Lett. 23, 1965–8 (1974)). The product is isolated by acidification and extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (3S,4S)-3-amino-4-hydroxypentane is isolated as a light yellow oil.

EXAMPLE 25
Production of (2S,3S)-2-amino-3-hydroxybutane

Five grams of (2S,3S)-2-methyl-3-hydroxybutyrate hydrazide are reacted with a solution of 5 grams of sodium nitrite in 100 ml of 5% $H_2SO_4$. The reaction mixture is maintained at a temperature of 0–5° C. for 1 hour, followed by extraction of the reaction mixture with ethyl acetate, basification of the resulting aqueous solution with NaOH, extraction with methyl t-butyl ether, drying of the extracts over $MgSO_4$, filtration, and the removal of solvent by rotary evaporation. The product (2S,3S)-2-amino-3-hydroxybutane is isolated as a light yellow oil.

EXAMPLE 26
Production of (1S,2S)-1-hydroxy-2-carboethoxyindane

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4 \cdot 7H_2O$ (0.5 gram), $NaNO_3$ (2 grams), $FeSO_4 \cdot 7H_2O$ (0.02 gram), and KCl (0.5 gram) with rotary shaking at 25° C. Two grams of 2-carboethoxy-1-indanone is dissolved in 2 ml of 95% ethanol the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of (1S,2S)-1-hydroxy-2-carboethoxyindane as a yellow oil. The chiral purity of the product is greater than 98% as judged by chiral chromatography.

EXAMPLE 27
Production of (1S,2S)-1-hydroxy-2-carboethoxy-5 fluoroindane

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4 \cdot 7H_2O$ (0.5 gram), $NaNO_3$ (2 grams), $FeSO_4 \cdot 7H_2O$ (0.02 gram), and KCl (0.5 gram) with rotary shaking at 25° C. Two grams of 5-fluoro-2-carboethoxy-1-indanone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of (1S,2S)-1-hydroxy-2-carboethoxy-5-fluoroindane as a yellow oil. The chiral purity of the product is greater than 98% as judged by chiral chromatography.

EXAMPLE 28
Production of (1S,2S)-1-hydroxy-2-carboethoxy-5-methoxyindane

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4 \cdot 7H_2O$ (0.5 gram), $NaNO_3$ (2 grams), $FeSO_4 \cdot 7H_2O$ (0.02 gram), and KCl (0.5 gram) with rotary shaking at 25° C. Two grams of 5-methoxy-2-carboethoxy-1-indanone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of (1S,2S)-1-hydroxy-2-carboethoxy-5-methoxyindane as a yellow oil. The chiral purity of the product is greater than 98% as judged by chiral chromatography.

EXAMPLE 29
Alternative production of (1S,2S)-1-hydroxy-2-carboethoxyindane *Rhizopus arrhizus* (ATCC 11145) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4 \cdot 7H_2O$ (0.5 gram), $NaNO_3$ (2 grams), $FeSO_4 \cdot 7H_2O$ (0.02 gram), and KCl (0.5 gram) with rotary shaking at 25° C. Two grams of 2-carboethoxy-1-indanone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.6 grams of (1S,2S)-1-hydroxy-2-carboethoxyindane as a yellow oil. The chiral purity of the product is shown to be greater than 95% as judged by chiral chromatography.

EXAMPLE 30
Production of (1S,2R)-1-hydroxy-2-carboethoxyindane

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 2-carboethoxy-1-indanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.8 grams of a yellowish oil containing (1S,2R)-1-hydroxy-2-carboethoxyindane (>95% enantiomeric excess as judged by chiral chromatography).

EXAMPLE 31
Production of (1S,2R)-1-hydroxy-2-carboethoxy-5-fluoroindane

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 5-fluoro-2-carboethoxy-1-indanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave a yellowish oil containing 1.5 grams of (1S,2R)-1-hydroxy-2-carboethoxy-5-fluoroindane (>95% enantiomeric excess as judged by chiral chromatography).

EXAMPLE 32
Production of (1S,2R)-1-hydroxy-2-carboethoxy-5-hydroxyindane

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 5-hydroxy-2-carboethoxy-1-indanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.5 grams of (1S,2R)-1-hydroxy-2-carboethoxy-5-hydroxyindane as a yellowish oil (>95% enantiomeric excess as judged by chiral chromatography).

EXAMPLE 33
Production of (1S,2R)-1-hydroxy-2-carboethoxy-5-carboxyethylindane Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 5-carboxyethyl-2-carboethoxy-1-indanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.5 grams of (1S,2R)-1-hydroxy-2-carboethoxy-5-carboxyethylindane as a yellowish oil (>95% enantiomeric excess as judged by chiral chromatography).

EXAMPLE 34
Conversion of (1S,2S)-1-hydroxy-2-carboethoxyindane to the hydrazide derivative (1S,2S)-1-hydroxy-2-carboethoxyindane (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCL, and the ethyl acetate solution is dried over $MgSO_4$, filtered, and rotary evaporated to leave 0.9 grams of the hydrazide of (1S,2S)-1-hydroxy-2-carboxyindane.

EXAMPLE 35
Conversion of (1S,2S)-1-hydroxy-2-carboethoxy-5-fluoroindane to the hydrazide derivative (1S,2S)-1-hydroxy-2-carboethoxy-5-fluoroindane (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-5-fluoroindane.

EXAMPLE 36
Conversion of (1S,2S)-1-hydroxy-2-carboethoxy-5-chloroindane to the hydrazide derivative (1S,2S)-1-hydroxy-2-carboethoxy-5-chloroindane (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl and the ethyl acetate solution is dried over $MgSO_4$, filtered, and rotary evaporated to leave 0.9 grams of the hydrazide of (1S,2S)-1-hydroxy-2-carboxy-5-chloroindane.

EXAMPLE 37
Conversion of (1S,2S)-1-hydroxy-2-carboethoxy-4,5,6,7-tetrafluoroindane to the hydrazide derivative (1S,2S)-1-hydroxy-2-carboethoxy-4,5,6,7-tetrafluoroindane (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-4,5,6,7-tetrafluoroindane.

EXAMPLE 38
Conversion of (1S,2S)-1-hydroxy-2-carboethoxy-5-hydroxyindane to the hydrazide derivative (1S,2S)-1-hydroxy-2-carboethoxy-5-hydroxyindane (1 gram) is dissolved in 5 ml of absolute ethanol followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-5-hydroxyindane.

EXAMPLE 39

Conversion of (1S,2S)-1-hydroxy-2-carboethoxy-5-methoxyindane to the hydrazide derivative (1S,2S)-1-hydroxy-2-carboethoxy-6-methoxytetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-5-methoxyindane.

EXAMPLE 40

Conversion of (1S,2R)-1-hydroxy-2-carboethoxyindane to the hydrazide derivative (1S,2R)-1-hydroxy-2-carboethoxyindane (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2R)-1-hydroxy-2-carboxyindane.

EXAMPLE 41

Conversion of (1S,2R)-1-hydroxy-2-carboethoxy-5-hydroxyindane to the hydrazide derivative (1S,2R)-1-hydroxy-2-carboethoxy-5-hydroxyindane (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-5-hydroxyindane.

EXAMPLE 42

Conversion of (1S,2R)-1-hydroxy-2-carboethoxy-5-fluoroindane to the hydrazide derivative (1S,2R)-1-hydroxy-2-carboethoxy-5-fluoroindane (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-5-fluoroindane.

EXAMPLE 43

Microbial production of the hydrazide of (1S,2S)-1-hydroxy-2-carboxyindane by stereospecific reduction of 2-carboxy-1-indanone hydrazide

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxy-1-indanone hydrazide, produced by the reaction of 2-carboethoxy-1-tetralone with hydrazine, is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1S,2S)-1-hydroxy-2-carboxyindane hydrazide.

EXAMPLE 44

Production of (1S,2S)-1-hydroxy-2-carboxamidoindane by microbial reduction of the corresponding 2-carboxamido-1-indanone

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxamido-1-indanone is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1S,2S)-1-hydroxy-2-carboxamidoindane.

EXAMPLE 45

Production of (1S,2R)-1-hydroxy-2-carboxamidoindane

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 2-carboxamido-1-indanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of a light yellow solid containing (1S,2R)-1-hydroxy-2-carboxamidoindane.

EXAMPLE 46
Production of the hydroxamic acid of (1S,2R)-1-hydroxy-2-carboxyindane (1S,2R)-1-hydroxy-2-carboethoxyindane (1 gram) is dissolved in 5 ml of absolute ethanol, followed by the addition of 0.5 gram of hydroxylamine. The solution is heated to reflux, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxyindane.

EXAMPLE 47
Enzymatic production of the hydroxamic acid of (1S,2R)-1-hydroxy-2-carboxyindane (1S,2R)-1-hydroxy-2-carboethoxyindane (1 gram) is dissolved in 5 ml of t-butyl methyl ether, followed by the addition of 0.5 gram of hydroxylamine. Lipase from *Candida rugosa* (0.5 g, Sigma L1754) is added, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxyindane.

EXAMPLE 48
Alternative production of the hydroxamic acid of (1S,2R)-1-hydroxy-2-carboxyindane by microbial reduction of the corresponding hydroxamic acid of 2-carboethoxy-1-indanone

*Rhizopus arrhizus* (ATCC 11145) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxy-1-indanone hydroxamic acid, produced by the reaction of 2-carboethoxy-1-tetralone with hydroxylamine, is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing as the major product (1S,2R)-1-hydroxy-2-carboxyindane hydroxamic acid.

EXAMPLE 49
Microbial production of the hydrazide of (2S,3S)-2 ethyl-3-hydroxybutyrate by stereospecific reduction of 2-ethylacetoacetate hydrazide

*Geotrichum candidum* (ATCC 34614) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-ethylacetoacetate hydrazide, produced by the reaction of ethyl acetoacetate with hydrazine, is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the dear yellow filtrate is extracted with ethyl acetate (4×200 ml). The extracts are combined, dried over $MgSO_4$, filtered, and rotary evaporated to leave 1 gram of (2S,3S)-2 ethyl-3-hydroxybutyrate hydrazide as a yellowish solid.

EXAMPLE 50
Production of (2S,3S)-2 ethyl-3-hydroxybutyramide by microbial reduction of the corresponding 2-ethylacetoacetamide

*Geotrichum candidum* (ATCC 34614) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-ethyl-3-ketobutyramide is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of (2S,3S)-2 ethyl-3-hydroxybutyramide as a yellowish solid.

EXAMPLE 51
Production of S-3 hydroxybutyramide

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of acetoacetamide is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of (S)-3-hydroxybutyramide as a light yellow solid.

EXAMPLE 52
Production of the hydroxamic acid of (2S,3S)-2 ethyl-3-hydroxybutyrate (2S,3S)-Ethyl 2 ethyl-3-hydroxybutyrate (1 gram) is dissolved in 5 ml of absolute ethanol followed by the addition of 0.5 gram of hydroxylamine. The solution is heated to reflux, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over MgSO$_4$, filtered, and rotary evaporated to leave 0.8 grams of the hydroxamic acid derivative of (2S,3S)-2 ethyl-3-hydroxybutyrate.

EXAMPLE 53
Enzymatic production of the hydroxamic acid of (2S,3S)-2 ethyl-3-hydroxybutyrate (2S,3S)-Ethyl 2 ethyl-3-hydroxybutyrate (1 gram) is dissolved in 5 ml of t-butyl methyl ether, followed by the addition of 0.5 gram of hydroxylamine. Lipase from *Candida rugosa* (0.5 g, Sigma L1754) is added, and the progress of the reaction is followed by thin layer chromatography. After the reaction is judged complete, the ethanol is evaporated and the resulting residue redissolved in ethyl acetate. Hydroxylamine is removed by extraction with 1% HCL, and the ethyl acetate solution is dried over MgSO$_4$, filtered, and rotary evaporated to leave 0.8 grams of the hydroxamic acid derivative of (2S,3S)-2 ethyl-3-hydroxybutyrate.

EXAMPLE 54
Alternative production of the hydroxamic acid of (2S,3S)-2 ethyl-3-hydroxybutyrate by microbial reduction of the corresponding hydroxamic acid of 2-ethylacetoacetate

*Geotrichum candidum* (ATCC 34614) is cultured according to the method of Buisson and Azerad (Tet. Lett. 27, 2631–2634 (1986), herein incorporated by reference) in one liter of a medium of glucose (30 grams), KH$_2$PO$_4$ (1 gram), K$_2$HPO$_4$ (2 grams), corn steep liquor (10 grams) MgSO$_4$.7H$_2$O (0.5 gram), NaNO$_3$ (2 grams), FeSO$_4$.7H$_2$O (0.02 gram), and KCl (0.5 gram) with rotary shaking at 25° C. Two grams of 2-ethylacetoacetate hydroxamic acid, produced by the reaction of ethyl acetoacetate with hydroxylamine, is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1 gram of (2S,3S)-2 ethyl-3-hydroxybutyrate hydroxamic acid as a yellowish solid.

EXAMPLE 55
Alternative production of ethyl (2S,3S)-2-ethyl-3-hydroxybutyrate Two grams of ethyl 2-ethyl acetoacetate is dissolved in 2 ml of 95% ethanol, and the resulting solution is added to a solution of alcohol dehydrogenase (500 units from *Rhizopus arrhizus* (ATCC 11145) containing potassium phosphate buffer, 100 mM, pH 7.0. NAD+ (100 mg) is added to the solution along with 1 gram of sodium formate and 100 units of formate dehydrogenase (Boehringer Mannheim). for recycling of the NAD+ cofactor. The reaction is followed by TLC (staining with anisaldehyde) to monitor the consumption of starting material and the production of product alcohol. After approximately 48 hours the reaction is judged complete, and the reaction is terminated by removing from the shaker. The resulting solution is extracted with ethyl acetate (4×200 ml). The extracts are combined, dried over MgSO$_4$, filtered, and rotary evaporated to leave 1.8 grams of (2S,3S)-2-ethyl-3-hydroxybutyrate as a light yellow oil. The chiral purity of the product is greater than 99% as judged by chiral chromatography.

EXAMPLE 56
Production of (1S,2R)-ethyl 2-hydroxycyclopentanecarboxylate

Twenty-five grams of bakers' yeast (*Saccharomyces cerevisiae,* Sigma Chemical Company, type II) are suspended in 100 ml of sterilized tap water in a conical flask, and the mixture is placed on an orbital shaker (220 rpm) at 30° C. for 1 hour to activate the yeast. One gram of ethyl 2-oxocyclopentanecarboxylate is added, shaking is resumed, and progress of the reaction is monitored by TLC (staining with anisaldehyde). After approximately 100 hours the reaction is judged complete, and the reaction is terminated by removing from the shaker and adding 20–30 grams of Celite. The resulting suspension is suction filtered through a pad of Celite and the clear yellow filtrate is extracted with diethyl ether (4×100 ml). The extracts are combined, dried over MgSO$_4$, filtered, and rotary evaporated to leave 0.7 grams of octyl (1R,2S)-ethyl 2-hydroxycyclopentanecarboxylate as a yellowish oil (70% yield).

EXAMPLE 57
Production of (1S,2S)-1-hydroxy-2-carboethoxytetralin

*Colletotrichum gloeosporioides* is cultured according to the method of Buisson and Azerad (Tet. Lett. 27, 2631–2634 (1986), herein incorporated by reference) in one liter of a medium of glucose (30 grams), KH$_2$PO$_4$ (1 gram), K$_2$HPO$_4$ (2 grams), corn steep liquor (10 grams) MgSO$_4$.7H$_2$O (0.5 gram), NaNO$_3$ (2 grams), FeSO$_4$.7H$_2$O (0.02 gram), and KCl (0.5 gram) with rotary shaking at 25° C. Two grams of 2-carboethoxy-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.7 grams of a yellow oil containing (1S,2S)-1-hydroxy-2-carboethoxytetralin. The chiral purity of the product is greater than 95% as judged by chiral chromatography.

EXAMPLE 58
Production of (1S,2S)-1-hydroxy-2-carboethoxy-6-fluorotetralin

*Colletotrichum gloeosporioides* is cultured according to the method of Buisson and Azerad (Tet. Lett. 27, 2631–2634 (1986), herein incorporated by reference) in one liter of a medium of glucose (30 grams), KH$_2$PO$_4$ (1 gram), K$_2$HPO$_4$ (2 grams), corn steep liquor (10 grams) MgSO$_4$.7H$_2$O (0.5 gram), NaNO$_3$ (2 grams), FeSO$_4$.7H$_2$O (0.02 gram), and KCl (0.5 gram) with rotary shaking at 25° C. Two grams of 6-fluoro-2-carboethoxy-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of a yellow oil containing (1S,2S)-1-hydroxy-2-carboethoxy-6-fluorotetralin. The chiral purity of the product is greater than 98% as judged by chiral chromatography.

EXAMPLE 59

Production of (1S,2S)-1-hydroxy-2-carboethoxy-6-chlorotetralin

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 6-chloro-2-carboethoxy-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of(1S,2S)-1-hydroxy-2-carboethoxy-6-chlorotetralin as a yellow oil. The chiral purity of the product is greater than 98% as judged by chiral chromatography.

EXAMPLE 60

Production of (1S,2S)-1-hydroxy-2-carboethoxy-5,6,7,8-tetrafluorotetralin

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 5,6,7,8-tetrafluoro-2-carboethoxy-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of a yellow oil containing (1S,2S)-1-hydroxy-2-carboethoxy-5,6,7,8-tetrafluorotetralin. The chiral purity of the product is greater than 98% as judged by chiral chromatography.

EXAMPLE 61

Production of (1S,2S)-1-hydroxy-2-carboethoxy-6-hydroxytetralin

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 6-hydroxy-2-carboethoxy-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of a yellow oil containing (1S,2S)-1-hydroxy-2-carboethoxy-6-hydroxytetralin. The chiral purity of the product is greater than 95% as judged by chiral chromatography.

EXAMPLE 62

Production of (1S,2S)-1-hydroxy-2-carboethoxy-6-methoxytetralin

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 6-methoxy-2-carboethoxy-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.7 grams of a yellow oil containing (1S,2S)-1-hydroxy-2-carboethoxy-6-methoxytetralin. The chiral purity of the product is greater than 95% as judged by chiral chromatography.

EXAMPLE 63

Alternative production of (1S,2S)-1-hydroxy-2-carboethoxytetralin

*Rhizopus arrhizus* (ATCC 11145) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboethoxy-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.6 grams of a yellow oil containing (1S,2S)-1-hydroxy-2-carboethoxytetralin. The chiral purity of the product is shown to be greater than 95% as judged by chiral chromatography.

EXAMPLE 64
Production of (1S,2R)-1-hydroxy-2-carboethoxytetralin

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 2-carboethoxy-1-tetralone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.8 grams of a yellow oil containing (1S,2R)-1-hydroxy-2-carboethoxytetralin (>95% enantiomeric excess as judged by chiral chromatography).

EXAMPLE 65
Production of (1S,2R)-1-hydroxy-2-carboethoxy-6-fluorotetralin

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 6-fluoro-2-carboethoxy-1-tetralone is dissolved in 2 ml of 95% ethanol the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.8 grams of a yellow oil containing (1S,2R)-1-hydroxy-2-carboethoxy-6-fluorotetralin (>95% enantiomeric excess as judged by chiral chromatography).

EXAMPLE 66
Production of (1S,2R)-1-hydroxy-2-carboethoxy-6-hydroxytetralin

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 6-hydroxy-2-carboethoxy-1-tetralone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.8 grams of a yellow oil containing (1S,2R)-1-hydroxy-2-carboethoxy-6-hydroxytetralin (>95% enantiomeric excess as judged by chiral chromatography).

EXAMPLE 67
Production of (1S,2R)-1-hydroxy-2-carboethoxy-6-carboxyethyltetralin Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 6-carboxyethyl-2-carboethoxy-1-tetralone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over MgSO$_4$, filtered, and rotary evaporated to leave 1.8 grams of a yellow oil containing (1S,2R)-1-hydroxy-2-carboethoxy-6-carboxyethyltetralin (>95% enantiomeric excess as judged by chiral chromatography).

EXAMPLE 68
Conversion of (1S,2S)-1-hydroxy-2-carboethoxytetralin to the hydrazide derivative (1S,2S)-1-hydroxy-2-carboethoxytetralin (1 gram) is dissolved in 5 ml of absolute ethanol followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over MgSO$_4$, filtered, and rotary evaporated to leave 0.9 grams of the hydrazide of (1S,2S)-1-hydroxy-2-carboxytetralin.

EXAMPLE 69
Conversion of (1S,2S)-1-hydroxy-2-carboethoxy-6-fluorotetralin to the hydrazide derivative (1S,2S)-1-hydroxy-2-carboethoxy-6-fluorotetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over MgSO$_4$, filtered, and rotary evaporated to leave 0.9 grams of the hydrazide of (1S,2S)-1-hydroxy-2-carboxy-6-fluorotetralin.

EXAMPLE 70
Conversion of (1S,2S)-1-hydroxy-2-carboethoxy-6-chlorotetralin to the hydrazide derivative (1S,2S)-1-hydroxy-2-carboethoxy-6-chlorotetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-6-chlorotetralin.

EXAMPLE 71
Conversion of (1S,2S)-1-hydroxy-2-carboethoxy-5,6,7,8-tetrafluorotetralin to the hydrazide derivative (1S,2S)-1-hydroxy-2-carboethoxy-5,6,7,8-tetrafluorotetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-5,6,7,8-tetrafluorotetralin.

EXAMPLE 72
Conversion of (1S,2S)-1-hydroxy-2-carboethoxy-6-hydroxytetralin to the hydrazide derivative (1S,2S)-1-hydroxy-2-carboethoxy-6-hydroxytetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-6-hydroxytetralin.

EXAMPLE 73
Conversion of (1S,2S)-1-hydroxy-2-carboethoxy-6-methoxytetralin to the hydrazide derivative (1S,2S)-1-hydroxy-2-carboethoxy-6-methoxytetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-6-methoxytetralin.

EXAMPLE 74
Conversion of (1S,2R)-1-hydroxy-2-carboethoxytetralin to the hydrazide derivative (1S,2R)-1-hydroxy-2-carboethoxytetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2R)-1-hydroxy-2-carboxytetralin.

EXAMPLE 75
Conversion of (1S,2R)-1-hydroxy-2-carboethoxy-6-hydroxytetralin to the hydrazide derivative (1S,2R)-1-hydroxy-2-carboethoxy-6-hydroxytetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-6-hydroxytetralin.

EXAMPLE 76
Conversion of (1S,2R)-1-hydroxy-2-carboethoxy-6-fluorotetralin to the hydrazide derivative (1S,2R)-1-hydroxy-2-carboethoxy-6-fluorotetralin (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2S)-1-hydroxy-2-carboxy-6-fluorotetralin.

EXAMPLE 77
Microbial production of the hydrazide of (1S,2S)-1-hydroxy-2-carboxytetralin by stereospecific reduction of 2-carboxy-1-tetralone hydrazide Colletotrichum gloeosporioides is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4 \cdot 7H_2O$ (0.5 gram), $NaNO_3$ (2 grams), $FeSO_4 \cdot 7H_2O$ (0.02 gram), and KCl (0.5 gram) with rotary shaking at 25° C. Two grams of 2-carboxy-1-tetralone hydrazide, produced by the reaction of 2-carboethoxy-1-tetralone with hydrazine, is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1S,2S)-1-hydroxy-2-carboxytetralin hydrazide.

EXAMPLE 78
Production of (1S,2S)-1-hydroxy-2-carboxamidotetralin by microbial reduction of the corresponding 2-carboxamido-1-tetralone Colletotrichum gloeosporioides is cultured according to the method of Buisson and Azerad (Tet. Lett. 27, 2631–2634

(1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxamido-1-tetralone is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1gram of a yellowish solid containing (1S,2S)-1-hydroxy-2-carboxamidotetralin.

EXAMPLE 79

Production of (1S,2R)-1-hydroxy-2-carboxamidotetralin

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 2-carboxamido-1-tetralone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of a light yellow solid containing (1S,2R)-1-hydroxy-2-carboxamidotetralin.

EXAMPLE 80

Production of the hydroxamic acid of (1S,2R)-1-hydroxy-2-carboxytetralin (1S,2R)-1-hydroxy-2-carboethoxytetralin (1 gram) is dissolved in 5 ml of absolute ethanol, followed by the addition of 0.5 gram of hydroxylamine. The solution is heated to reflux, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxytetralin.

EXAMPLE 81

Enzymatic production of the hydroxamic acid of (1S,2R)-1-hydroxy-2-carboxytetralin (1S,2R)-1-hydroxy-2-carboethoxytetralin (1 gram) is dissolved in 5 ml of t-butyl methyl ether, followed by the addition of 0.5 gram of hydroxylamine. Lipase from Candida rugosa (0.5 g, Sigma L1754) is added, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxytetralin.

EXAMPLE 82

Alternative production of the hydroxamic acid of (1S,2R)-1-hydroxy-2-carboxytetralin by microbial reduction of the corresponding hydroxamic acid of 2-carboethoxy-1-tetralone Rhizopus arrhizus (ATCC 11145) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep-liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxy-1-tetralone hydroxamic acid, produced by the reaction of 2-carboethoxy-1-tetralone with hydroxylamine, is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the dear yellow filtrate is extracted with ethyl acetate (4×200 ml). The extracts are combined, dried over $MgSO_4$, filtered, and rotary evaporated to leave 1 gram of a yellowish solid containing as the major product (1S,2R)-1-hydroxy-2-carboxytetralin hydroxamic acid.

EXAMPLE 83

Alternative production of ethyl (2S,3S)-2-ethyl-3-hydroxybutyrate

Two grams of ethyl 2-ethyl acetoacetate are dissolved in 2 ml of 95% ethanol, and the resulting solution is added to a solution of alcohol dehydrogenase (500 units from Rhizopus arrhizus (ATCC 11145) containing potassium phosphate buffer, 100 mM, pH 7.0. NAD+ (100 mg) is added to the solution along with 1 gram of sodium formate and 100 units of formate dehydrogenase (Boehringer Mannheim). for recycling of the NAD+ cofactor. The reaction is followed by TLC (staining with anisaldehyde) to monitor the consumption of starting material and the production of product alcohol. After approximately 48 hours the reaction is judged complete, and the reaction is terminated by removing from the shaker. The resulting solution is extracted with ethyl acetate (4×200 ml). The extracts are combined, dried over $MgSO_4$, filtered, and rotary evaporated to leave 1.8 grams of (2S,3S)-2-ethyl-3-hydroxybutyrate as a light yellow oil. The chiral purity of the product is greater than 99% as judged by chiral chromatography.

EXAMPLE 84

Production of (1S,2R)-ethyl 2-hydroxycyclopentanecarboxylate

Twenty-five grams of bakers' yeast (Saccharomyces cerevisiae, Sigma Chemical Company, type II) are suspended in 100 ml of sterilized tap water in a conical flask, and the mixture is placed on an orbital shaker (220 rpm) at 30° C. for 1 hour to activate the yeast. One gram of ethyl 2-oxocyclopentanecarboxylate is added, shaking is resumed, and progress of the reaction is monitored by TLC (staining with anisaldehyde). After approximately 100 hours the reaction is judged complete, and the reaction is terminated by removing from the shaker and adding 20–30 grams of Celite. The resulting suspension is suction filtered through a pad of Celite and the clear yellow filtrate is extracted with diethyl ether (4×100 ml). The extracts are combined, dried over $MgSO_4$, filtered, and rotary evaporated to leave 0.7 grams of octyl (1R,2S)-ethyl 2-hydroxycyclopentanecarboxylate as a yellowish oil (70% yield).

EXAMPLE 85
Conversion of ethyl (1R,2S)-2-hydroxycyclopentanecarboxylate to the hydrazide derivative Ethyl (1R,2S)-2-hydroxycyclopentanecarboxylate (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1R,2S)-2-hydroxycyclopentanecarboxylate.

EXAMPLE 86
Microbial production of the hydrazide of (1R,2S)-2-hydroxycyclopentanecarboxylate by stereospecific reduction of 2-oxocyclopentanecarboxylate hydrazide

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-oxocyclopentanecarboxylate hydrazide, produced by the reaction of ethyl 2 oxocyclopentanecarboxylate with hydrazine, is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1R,2S)-2-hydroxycyclopentanecarboxylate hydrazide.

EXAMPLE 87
Production of (1S,2S)-2-hydroxy-1-carboxamidocyclopentane by stereospecific reduction of 2-carboxamido-1-cyclopentanone

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxamido-1-cyclopentanone is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1S,2S)-2-hydroxy-1-carboxamidocyclopentane.

EXAMPLE 88
Production of (1S,2R)-2-hydroxy-1-carboxamidocyclopentane

Twenty grams of bakers' yeast (Sigma Chemical Company, type II) is suspended in an aqueous solution containing 30 grams of sucrose in a conical flask, and the mixture is placed on an orbital shaker (220 rpm) at 30° C. for 30 minutes to initiate fermentation. Two grams of 2-carboxamido-1-cyclopentanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of a light yellow solid containing (1S,2S)-2-hydroxy-1-carboxamidocyclopentane.

EXAMPLE 89
Production of the hydroxamic acid of (1S,2R)-1-hydroxy-2-carboxycyclopentane (1S,2R)-1-hydroxy-2-carboethoxycyclopentane (1 gram) is dissolved in 5 ml of absolute ethanol followed by the addition of 0.5 gram of hydroxylamine. The solution is heated to reflux, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxycyclopentane.

EXAMPLE 90
Enzymatic production of the hydroxamic acid of (1S,2R)-1-hydroxy-2-carboxycyclopentane (1S,2R)-1-hydroxy-2-carboethoxycyclopentane (1 gram) is dissolved in 5 ml of t-butyl methyl ether, followed by the addition of 0.5 gram of hydroxylamine. Lipase from *Candida rugosa* (0.5 g, Sigma L1754) is added, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxycyclopentane.

EXAMPLE 91
Alternative production of the hydroxamic acid of (1S,2R)-1-hydroxy-2-carboxycyclopentane by microbial reduction of the hydroxamic acid of 2-carboxy-1-cyclopentanone

*Rhizopus arrhizus* (ATCC 11145) is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxy-1-cyclopentanone hydroxamic acid is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing as the major product (1S,2R)-1-hydroxy-_2-carboxycyclopentane hydroxamic acid.

EXAMPLE 92
Conversion of ethyl (1R,2S)-2-hydroxycyclohexanecarboxylate to the hydrazide derivative Ethyl (1R,2S)-2-hydroxycyclohexanecarboxylate (1 gram) is dissolved in 5 ml of absolute ethanol, followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1R,2S)-2-hydroxycyclohexanecarboxylate.

EXAMPLE 93
Microbial production of the hydrazide of (1S,2S)-2-hydroxycyclohexanecarboxylate by stereospecific reduction of 2-oxocyclohexanecarboxylate hydrazide

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-oxocyclopentanecarboxylate hydrazide is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1S,2S)-2-hydroxycyclohexanecarboxylate hydrazide.

EXAMPLE 94
Production of (1S,2S)-2-hydroxy-1-carboxamidocyclohexane by stereospecific reduction of 2-carboxamido-1-cyclohexanone

*Colletotrichum gloeosporioides* is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxamido-1-cyclohexanone is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1S,2S)-2-hydroxy-1-carboxamidocyclohexane.

EXAMPLE 95
Production of (1S,2R)-2-hydroxy-1-carboxamidocyclohexane

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 2-carboxamido-1-cyclohexanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of a light yellow solid containing (1S,2S)-2-hydroxy-1-carboxamidocyclohexane.

EXAMPLE 96
Production of the hydroxamic acid of (1S,2R)-1-hydroxy-2-carboxycyclohexane (1S,2R)-1-hydroxy-2-carboethoxycyclohexane (1 gram) is dissolved in 5 ml of absolute ethanol, followed by the addition of 0.5 gram of hydroxylamine. The solution is heated to reflux, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxycyclohexane.

EXAMPLE 97
Enzymatic production of the hydroxamic acid of (1S,2R)-1-hydroxy-2-carboxycyclohexane (1S,2R)-1-hydroxy-2-carboethoxycyclohexane (1 gram) is dissolved in 5 ml of t-butyl methyl ether, followed by the addition of 0.5 gram of hydroxylamine. Lipase from *Candida rugosa* (0.5 g, Sigma L1754) is added, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1S,2R)-1-hydroxy-2-carboxycyclohexane.

EXAMPLE 98
Alternative production of the hydroxamic acid of (1S,2R)-1-hydroxy-2-carboxycyclohexane by microbial reduction of the corresponding hydroxamic acid of 2-carboethoxy-1-cyclohexanone

*Rhizopus arrhizus* (ATCC 11145) is cultured according to the method of Buisson and Azerad (Tet. Lett. 27, 2631–2634

(1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 2-carboxy-1-cyclohexanone hydroxamic acid is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing as the major product (1S,2R)-1-hydroxy-2-carboxycyclohexane hydroxamic acid.

EXAMPLE 99
Conversion of (1S,2R)-1-carboethoxy-2-hydroxyindane to the hydrazide derivative (1S,2R)-1-carboethoxy-2-hydroxyindane (1 gram) is dissolved in 5 ml of absolute ethanol followed by the addition of 0.5 gram of hydrazine. The solution is heated to reflux, and the progress of the reaction is followed by thin layer chromatography. After the reaction is judged complete, the ethanol is evaporated and the resulting residue redissolved in ethyl acetate. Hydrazine is removed by extraction with 1% HCl, and the ethyl acetate solution is dried over $MgSO_4$, filtered, and rotary evaporated to leave 0.9 grams of the hydrazide of (1S,2R)-1-carboxy-2-hydroxyindane.

EXAMPLE 100
Production of (1S,2S)-2-hydroxy-1-carboxamidoindane by stereospecific reduction of 1-carboxamido-2-indanone Colletotrichum gloeosporioides is cultured according to the method of Buisson and Azerad (Tet. Lett. 27, 2631–2634 (1986), herein incorporated by reference) in one liter of a medium of glucose (30 grams), $KH_2PO_4$ (1 gram), $K_2HPO_4$ (2 grams), corn steep liquor (10 grams) $MgSO_4.7H_2O$ (0.5 gram), $NaNO_3$ (2 grams), $FeSO_4.7H_2O$ (0.02 gram), and KCl (0.5 gram) with rotary shaking at 25° C. Two grams of 1-carboxamido-2-indanone is dissolved in 2 ml of 95% ethanol, the resulting solution is added to the culture, and shaking is resumed. The reaction is followed by TLC (staining with anisaldehyde) to monitor the consumption of starting material and the production of product alcohol. After 48–72 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1 gram of a yellowish solid containing (1S,2S)-1-carboxamido-2-hydroxyindane.

EXAMPLE 101
Production of (1R,2S)-1-carboxamido-2-hydroxyindane

Twenty grams of bakers' yeast (Sigma Chemical Company, type II) are suspended in an aqueous solution containing 30 grams of sucrose in a conical flask, and the mixture is placed on an orbital shaker (220 rpm) at 30° C. for 30 minutes to initiate fermentation. Two grams of 1-carboxamido-2-indanone is dissolved in 2 ml of 95% ethanol, the resulting solution is added to the fermenting yeast, and shaking is resumed. The reaction is followed by TLC (staining with anisaldehyde) to monitor the consumption of starting material and the production of product alcohol. After approximately 48 hours the reaction is judged complete, and the reaction is terminated by removing from the shaker and adding 20–30 grams of Celite. The resulting suspension is suction filtered through a pad of Celite and the clear yellow filtrate is extracted with ethyl acetate (4×200 ml). The extracts are combined, dried over $MgSO_4$, filtered, and rotary evaporated to leave 1.4 grams of a light yellow solid containing (1S,2S)-1-carboxamido-2-hydroxyindane as the major product.

EXAMPLE 102
Production of the hydroxamic acid of (1R,2S)-1-carboxy-2-hydroxyindane (1R,2S)-1-carboethoxy-2-hydroxyindane (1 gram) is dissolved in 5 ml of absolute ethanol, followed by the addition of 0.5 gram of hydroxylamine. The solution is heated to reflux, and the progress of the reaction is followed by thin layer chromatography. After the reaction is judged complete, the ethanol is evaporated and the resulting residue redissolved in ethyl acetate. Hydroxylamine is removed by extraction with 1% HCl, and the ethyl acetate solution is dried over $MgSO_4$, filtered, and rotary evaporated to leave 0.8 grams of the hydroxamic acid derivative of (1R,2S)-1-carboxy-2-hydroxyindane.

EXAMPLE 103
Production of (1S,2R)-1-amino-2-indanol

The hydrazide of (1S,2R)-1-carboxy-2-hydroxyindane (0.5 gram) is reacted with a solution of 0.5 grams of sodium nitrite in 10 ml of 5% $H_2SO_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (1S,2R)-1-amino-2-indanol is isolated as a light yellow oil.

EXAMPLE 104
Production of (1S,2R)-1-amino-2-indanol by a modified Lossen Rearrangement One gram of the hydroxamic acid of (1R,2S)-1-carboxy-2-hydroxyindane is reacted with equimolar amounts of diethyl azodicarboxylate and triphenylphosphine in tetrahydrofuran at room temperature using the procedure of Bittner, Grinberg and Kartoon (Tet. Lett. 23, 1965–8 (1974)). The product is isolated by acidification and extraction of the reaction mixture with ethyl acetate, followed by basification of the resulting aqueous solution with NaOH, extraction with methyl t-butyl ether, drying of the extracts over $MgSO_4$, filtration, and the removal of solvent by rotary evaporation. The product (1S,2R)-1-amino-2-indanol is isolated as a light yellow oil.

EXAMPLE 105
Production of (1S,2S)-2-amino-1-indanol by a modified Lossen Rearrangement One gram of the hydroxamic acid of(1S,2S)-2-carboxy-1-hydroxyindane is reacted with equimolar amounts of diethyl azodicarboxylate and triphenylphosphine in tetrahydrofuran at room temperature using the procedure of Bittner, Grinberg and Kartoon (Tet. Lett. 23, 1965–8 (1974)). The product is isolated by acidification and extraction of the reaction mixture with ethyl acetate, followed by basification of the resulting aqueous solution with NaOH, extraction with methyl t-butyl ether, drying of the extracts over MgSO$_4$, filtration, and the removal of solvent by rotary evaporation. The product (1S,2S)-2-amino-1-indanol is isolated as a light yellow oil.

EXAMPLE 106
Production of (1S,2S)-1-hydroxy-2-aminotetralin by a modified Lossen Rearrangement One gram of the hydroxamic acid of (1S,2S)-1-hydroxy-2-carboxyteralin is reacted with equimolar amounts of diethyl azodicarboxylate and triphenylphosphine in tetrahydrofuran at room temperature using the procedure of Bittner, Grinberg and Kartoon (Tet. Lett. 23, 1965–8 (1974)). The product is isolated by acidification and extraction of the reaction mixture with ethyl acetate, followed by basification of the resulting aqueous solution with NaOH, extraction with methyl t-butyl ether, drying of the extracts over MgSO$_4$, filtration, and the removal of solvent by rotary evaporation. The product (1S,2S)-1-hydroxy-2-aminotetralin is isolated as a light yellow oil.

EXAMPLE 107
Production of (1S,2R)-1-hydroxy-2-aminotetralin by a modified Lossen Rearrangement One gram of the hydroxamic acid of (1S,2R)-2-carboxy-1-hydroxytetralin is reacted with equimolar amounts of diethyl azodicarboxylate and triphenylphosphine in tetrahydrofuran at room temperature using the procedure of Bittner, Grinberg and Kartoon (Tet. Lett. 23, 1965–8 (1974)). The product is isolated by acidification and extraction of the reaction mixture with ethyl acetate, followed by basification of the resulting aqueous solution with NaOH, extraction with methyl t-butyl ether, drying of the extracts over MgSO$_4$, filtration, and the removal of solvent by rotary evaporation. The product (1S,2R)-1-hydroxy-2-aminotetralin is isolated as a light yellow oil.

EXAMPLE 108
Production of (1S,2R)-1-hydroxy-2-aminotetralin

The hydrazide of (1S,2R)-1-hydroxy-2-carboxyindane (0.5 gram) is reacted with a solution of 0.5 grams of sodium nitrite in 10 ml of 5% H$_2$SO$_4$. The reaction mixture is maintained for 1 hour at 0–5° C., followed extraction of the reaction mixture with ethyl acetate, followed by basification of the resulting aqueous solution with NaOH, extraction with methyl t-butyl ether, drying of the extracts over MgSO$_4$, filtration, and the removal of solvent by rotary evaporation. The product (1S,2R)-1-hydroxy-2-aminotetralin is isolated as a light yellow oil.

What is claimed is:

1. A composition comprising a compound having a formula selected from the group consisting of formulae 1 to 16:

(1)

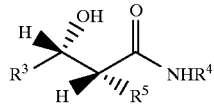

(2)

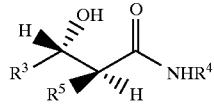

(3)

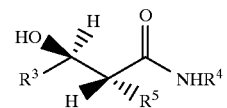

(4)

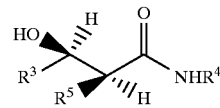

(5)

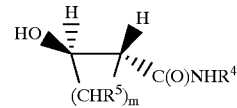

(6)

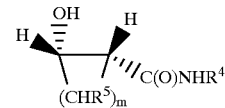

(7)

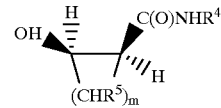

(8)

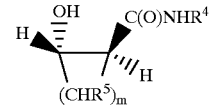

(9)

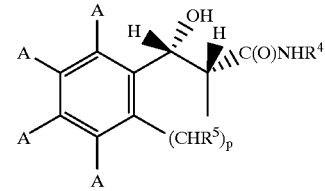

(10)

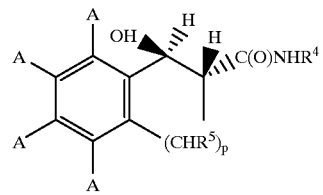

(11)

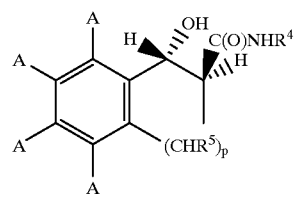

-continued

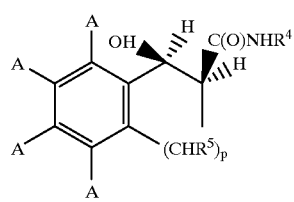
(12)

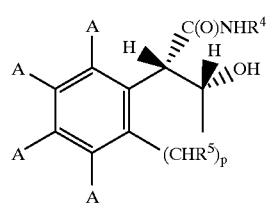
(13)

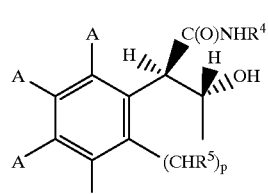
(14)

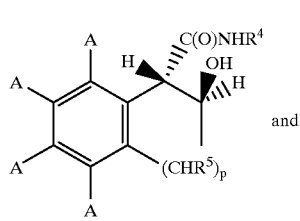
(15)

and

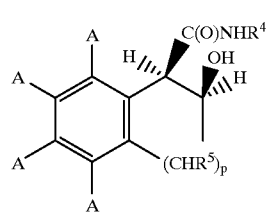
(16)

wherein:

$R^3$ is selected from the group consisting of alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic;

R is OH;

each $R^5$ is independently selected from the group consisting of hydrogen, alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic, with the proviso that, when the compound has a formula selected from formulae 1 to 4, $R^5$ is not hydrogen;

A is selected from the group consisting of H, F, Cl, Br, I, OH, $OCH_3$, alkyl, carboxy-substituted alkyl, hydroxy-substituted alkyl, halogen-substituted alkyl, aryl, carboxy-substituted aryl, hydroxy-substituted aryl, halogen-substituted aryl, and heterocyclic;

m is a number ranging from 1 to 6; and p is a number ranging from 0 to 6.

2. The composition of claim 1 comprising a compound having a formula selected from the group consisting of:

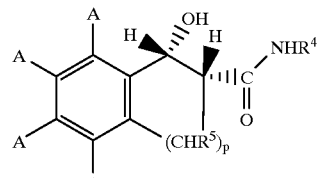

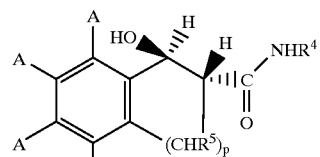

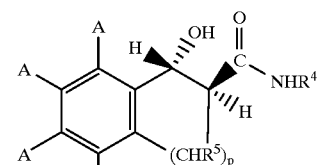

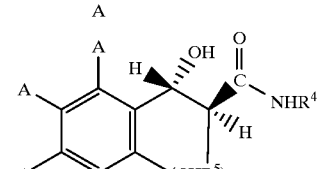

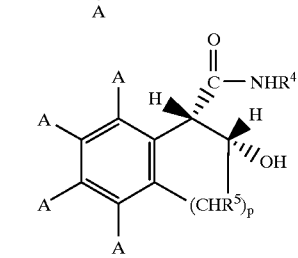

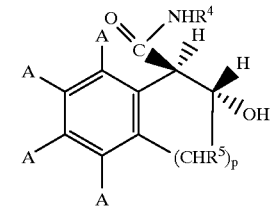

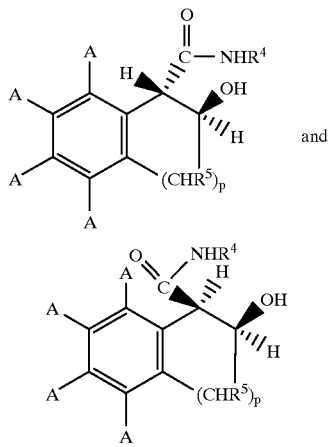

3. The composition of claim 2, wherein p is 1 or 2.

4. The composition of claim 1 comprising a compound having a formula selected from the group consisting of:

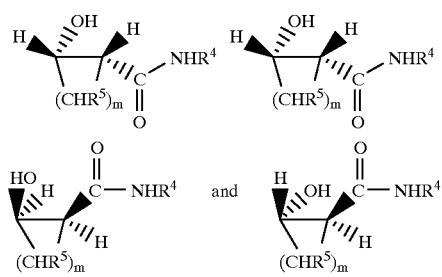

5. The composition of claim 4, wherein m is 3 or 4.

6. The composition of claim 1 comprising a compound having a formula selected from the group consisting of:

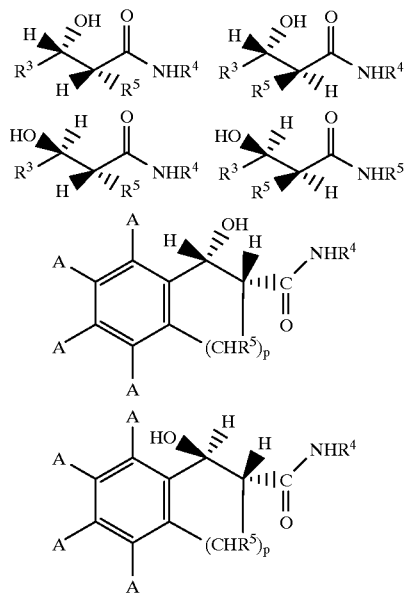

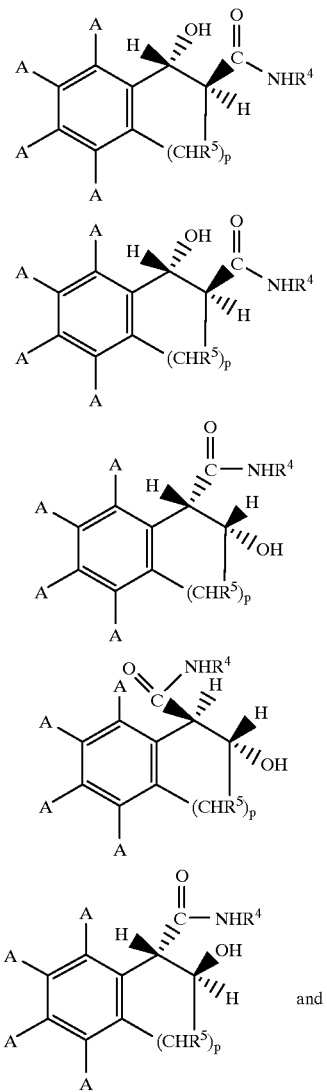

7. The composition of claim 1, wherein $R^5$ is selected from the group consisting of alkyl, aryl, benzyl and alkenyl.

8. The composition of claim 1 wherein $R^3$ is selected from the group consisting of alkyl, aryl, benzyl and alkenyl.

9. The composition of claim 1, comprising at least 90% of a single stereoisomer.

10. The composition of claim 1, comprising at least 98% of a single stereoisomer.

11. A composition comprising a compound having a formula selected from the group consisting of formulae 1 to 4 and 9 to 16:

wherein:
R³ is selected from the group consisting of alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic;

R is NH₂;

each R⁵ is independently selected from the group consisting of hydrogen, alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic, with the proviso that, when the compound has a formula selected from formulae 1 to 4, R⁵ is not hydrogen;

A is selected from the group consisting of H, F, Cl, Br, I, OH, OCH₃, alkyl, carboxy-substituted alkyl, hydroxy-substituted alkyl, halogen-substituted alkyl, aryl, carboxy-substituted aryl, hydroxy-substituted aryl, halogen-substituted aryl, and heterocyclic; and p is a number ranging from 0 to 6.

12. A composition according to claim 11, comprising a compound having a formula selected from the group consisting of formulae 1 to 4.

13. A composition according to claim 11 comprising a compound having a formula selected from the group consisting of formulae 9 to 16.

14. A composition according to claim 13 wherein p is 1 or 2.

15. A composition according to claim 11, wherein R⁵ is selected from the group consisting of hydrogen, alkyl, aryl, benzyl and alkenyl.

16. A composition according to claim 12, wherein $R^3$ is selected from the group consisting of alkyl, aryl, benzyl and alkenyl.

17. A composition according to claim 11, comprising at least 90% of a single stereoisomer.

18. A composition according to claim 11, comprising at least 98% of a single stereoisomer.

19. A composition comprising a compound having a formula selected from the group consisting of formulae 9 to 16:

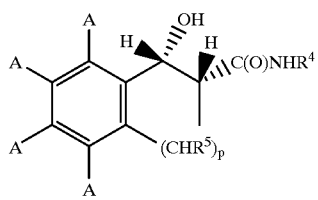
(9)

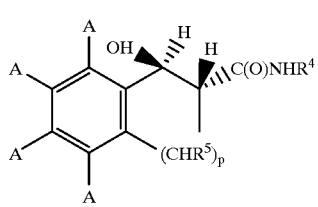
(10)

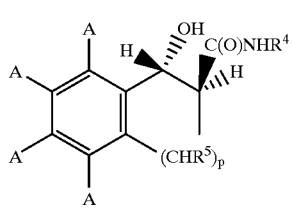
(11)

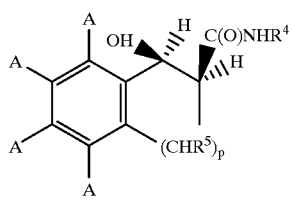
(12)

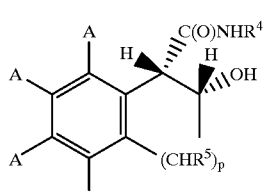
(13)

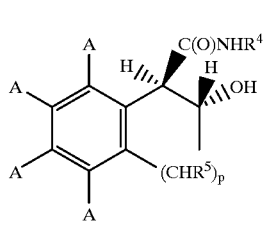
(14)

-continued

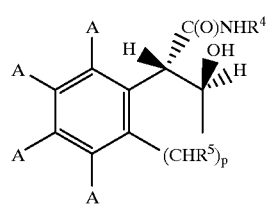
(15)

and

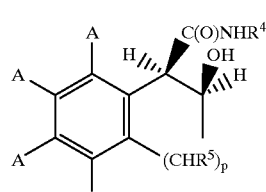
(16)

wherein:

$R^4$ is H;

each $R^5$ is indepdenently selected from the group consisting of hydrogen, alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic;

A is selected from the group consisting of H, F, Cl, Br, I, OH, $OCH_3$, alkyl, carboxy-substituted alkyl, hydroxy-substituted alkyl, halogen-substituted alkyl, aryl, carboxy-substituted aryl, hydroxy-substituted aryl, halogen-substituted aryl, and heterocyclic; and p is a number ranging from 0 to 6.

20. A composition according to claim 19 wherein p is 1 or 2.

21. A composition according to claim 19, wherein $R^5$ is selected from the group consisting of hydrogen, alkyl, aryl, benzyl and alkenyl.

22. A composition according to claim 19, comprising at least 90% of a single stereoisomer.

23. A composition according to claim 19, comprising at least 98% of a single stereoisomer.

24. A composition comprising a compound having a formula selected from the group consisting of formulae 1 to 4:

wherein:

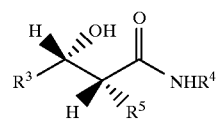
(1)

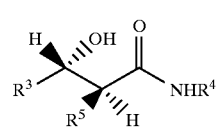
(2)

-continued (3)

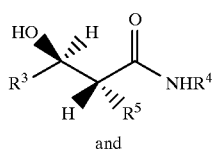

and (4)

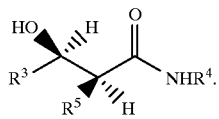

R³ is selected from the group consisting of alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic;

R⁴ is H; and

R⁵ is selected from the group consisting of aryl, halogen-substituted aryl hydroxy-substituted aryl, carboxy-substituted aryl, thio-substituted aryl, benzyl, halogen-substituted benzyl, thiophenyl, halogen-substituted thiophenyl, and heterocyclic.

25. A composition according to claim 24, wherein R³ is selected from the group consisting of alkyl, aryl, benzyl and alkenyl.

26. A composition according to claim 24, wherein R⁵ is selected from the group consisting of aryl and benzyl.

27. A composition according to claim 24, comprising at least 90% of a single stereoisomer.

28. A composition according to claim 24, comprising at least 98% of a single stereoisomer.

29. A composition comprising a compound having a formula selected from the group consisting of formulae 1 to 4:

wherein:

(1)

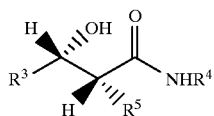

-continued (2)

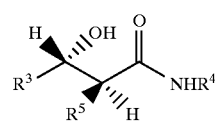

(3)

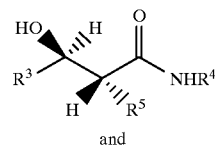

and (4)

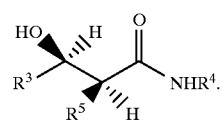

R³ is selected from the group consisting of aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic;

R⁴ is H; and

R⁵ is selected from the group consisting of alkyl, alkenyl, alkynyl, hydroxy-substituted alkyl, hydroxy-substituted alkenyl, halogen-substituted alkyl, halogen-substituted alkenyl, carboxy-substituted alkyl, thio-substituted alkyl, thio-substituted alkenyl, aryl, halogen-substituted aryl, hydroxy-substituted aryl, carboxy-substituted aryl, thio-substituted aryl, benzyl, halogen-substituted benzyl, thiophenyl, halogen-substituted thiophenyl, and heterocyclic.

30. A composition according to claim 29, wherein R⁵ is selected from the group consisting of alkyl, aryl, benzyl and alkenyl.

31. A composition according to claim 29, wherein R³ is selected from the group consisting of aryl and benzyl.

32. A composition according to claim 29, comprising at least 90% of a single stereoisomer.

33. A composition according to claim 29, comprising at least 98% of a single stereoisomer.

* * * * *